(12) United States Patent
Belgrader et al.

(10) Patent No.: US 7,785,869 B2
(45) Date of Patent: *Aug. 31, 2010

(54) SONICATION TO SELECTIVELY LYSE DIFFERENT CELL TYPES

(75) Inventors: Phillip I. Belgrader, Severna Park, MD (US); Bob Yuan, Belmont, CA (US)

(73) Assignee: Microfluidic Systems, Inc., Fremont, CA (US)

( * ) Notice: Subject to any disclaimer, the term of this patent is extended or adjusted under 35 U.S.C. 154(b) by 1093 days.

This patent is subject to a terminal disclaimer.

(21) Appl. No.: 11/352,108

(22) Filed: Feb. 9, 2006

(65) Prior Publication Data

US 2006/0134616 A1    Jun. 22, 2006

Related U.S. Application Data

(62) Division of application No. 10/943,613, filed on Sep. 17, 2004, now Pat. No. 7,541,166.

(60) Provisional application No. 60/504,072, filed on Sep. 19, 2003.

(51) Int. Cl.
  C12M 1/42     (2006.01)
  C12M 3/08     (2006.01)
  C12M 1/02     (2006.01)

(52) U.S. Cl. ............... 435/306.1; 435/288.5; 366/127; 241/2

(58) Field of Classification Search ............. 435/288.5, 435/306.1; 366/127; 241/2
See application file for complete search history.

(56) References Cited

U.S. PATENT DOCUMENTS

| | | | |
|---|---|---|---|
| 3,735,159 A | 5/1973 | Murry | |
| 4,275,166 A | 6/1981 | McCollough et al. | 435/227 |
| 4,610,961 A | 9/1986 | Guardino et al. | 435/34 |
| 4,666,595 A | 5/1987 | Graham | 210/222 |
| 5,048,520 A | 9/1991 | Vago | 128/24 A |
| 5,074,474 A | 12/1991 | Golz et al. | |
| 5,234,809 A | 8/1993 | Boom et al. | 435/91 |
| 5,707,799 A | 1/1998 | Hansmann et al. | 435/6 |
| 5,952,173 A | 9/1999 | Hansmann et al. | 435/6 |
| 6,100,084 A | 8/2000 | Miles et al. | 435/306.1 |
| 6,318,158 B1 | 11/2001 | Breen et al. | 73/64.56 |

(Continued)

FOREIGN PATENT DOCUMENTS

WO    WO 99/33559    7/1999

(Continued)

OTHER PUBLICATIONS

Office Action, U.S. Appl. No. 11/290,653, filed Nov. 29, 2005, 9 pages.

(Continued)

Primary Examiner—William H Beisner
(74) Attorney, Agent, or Firm—Haverstock & Owens LLP (57) ABSTRACT

A sonication apparatus is directed to a microfluidic-based system to automate differential extraction of specific cell types within a mixed sample. The microfluidic-based system includes a sonication module for selective cell lysis, separating means to eliminate centrifugation, high surface area pillar chip modules to purify DNA from a cell lysate, and microfluidic circuitry to integrate the steps in an automated platform.

16 Claims, 5 Drawing Sheets

U.S. PATENT DOCUMENTS

| | | |
|---|---|---|
| 6,374,684 B1 | 4/2002 | Dority .................... 73/864.81 |
| 6,391,541 B1 | 5/2002 | Petersen et al. ................. 435/5 |
| 6,540,895 B1 | 4/2003 | Spence et al. ............... 204/450 |
| 6,565,815 B1 | 5/2003 | Chang et al. ................ 422/198 |
| 6,578,659 B2 | 6/2003 | Manna et al. |
| 6,741,174 B2 | 5/2004 | Rhoades et al. ............ 340/540 |
| 7,005,982 B1 | 2/2006 | Frank .................... 340/539.26 |
| 7,006,923 B1 | 2/2006 | Rubin ......................... 702/19 |
| 7,082,369 B1 | 7/2006 | Rubin et al. .................. 702/19 |
| 7,106,442 B2 | 9/2006 | Silcott et al. ................ 356/338 |
| 7,491,527 B2 * | 2/2009 | Yuan et al. ............... 435/306.1 |
| 2001/0032666 A1 | 10/2001 | Jenson et al. ............... 136/256 |
| 2001/0036630 A1 | 11/2001 | Ibrahim ........................ 435/6 |
| 2002/0022261 A1 | 2/2002 | Anderson et al. ........ 435/287.2 |
| 2002/0039783 A1 | 4/2002 | McMillan et al. ........ 435/287.2 |
| 2002/0187547 A1 | 12/2002 | Taylor et al. |
| 2003/0215845 A1 | 11/2003 | Bille ............................. 435/6 |
| 2004/0197793 A1 | 10/2004 | Hassibi et al. ................. 435/6 |
| 2005/0019902 A1 | 1/2005 | Mathies et al. |
| 2005/0142565 A1 | 6/2005 | Samper et al. ................. 435/6 |
| 2005/0227275 A1 | 10/2005 | Jung et al. ..................... 435/6 |
| 2007/0026439 A1 | 2/2007 | Faulstich et al. |
| 2007/0116607 A1 | 5/2007 | Wang et al. ................... 422/83 |
| 2008/0050803 A1 | 2/2008 | Northrup et al. ......... 435/287.2 |
| 2008/0125330 A1 | 5/2008 | Cady et al. ................... 506/17 |

FOREIGN PATENT DOCUMENTS

WO      WO 03/070898 A2      8/2003

OTHER PUBLICATIONS

Office Action, mail date May 10, 2010, U.S. Appl. No. 11/509,868, filed Aug. 24, 2006, first named inventor: Amy J. Devitt, 21 pages.

* cited by examiner

SONICATION TO SELECTIVELY LYSE DIFFERENT CELL TYPES

RELATED APPLICATIONS

This Patent Application is a divisional of U.S. patent application Ser. No. 10/943,613 filed Sep. 17, 2004, now U.S. Pat. No. 7,541,166, the contents of which are hereby incorporated by reference. The parent U.S. patent application Ser. No. 10/943,613 claims priority of U.S. provisional application Ser. No. 60/504,072, filed Sep. 19, 2003, and entitled "Microfluidic Differential Extraction Instrument", by this same inventor. This application incorporates U.S. provisional application Ser. No. 60/504,072 in its entirety by reference.

FIELD OF THE INVENTION

The invention relates to a method and apparatus for lysing cells using sonication. In particular, the invention relates to selectively lysing different cell types using sonication.

BACKGROUND OF THE INVENTION

Cell lysis is the destruction, or disruption, of a cell's membrane or wall, which breaks open the cell and exposes its contents. Many techniques are available for the disruption of cells, including physical and detergent-based methods. Physical lysis often requires expensive, cumbersome equipment and involves protocols that are difficult to repeat due to variability in the apparatus. Detergent-based methods are often easier-to-use with more efficient protocols than physical methods.

Sonication is one method of physically lysing cells. Sonication uses pulsed, high frequency sound waves to agitate and lyse cells, bacteria, spores, and finely diced tissue. The sound waves are delivered using an apparatus with a vibrating probe that is immersed in the liquid cell suspension. Mechanical energy from the probe initiates the formation of microscopic vapor bubbles that form momentarily and implode, causing shock waves to radiate through the sample. The sonic energy delivered to a sample using this method is variable, and not repeatable for a necessary level of precision.

Cells can be treated with various agents to aid in the disruption process. For example, lysis can be promoted by suspending cells in a hypotonic buffer, which cause them to swell and burst more readily under physical shearing. Alternatively, processing can be expedited by treating cells with glass beads in order to facilitate the crushing of the cell walls.

The resistance of cells and viruses to lysis or disruption is based on the characteristics of the cell membrane, cell wall, or coat protein. The various chemical, enzymatic, and mechanical or physical approaches have been utilized to non-specifically lyse cells and viruses. However, in some applications, it is desirable to lyse one specific cell type or virus in a mixed sample of two or more cells and viruses. One such application is DNA typing.

DNA typing has been an invaluable tool for forensic science. Applications including linking a suspect to a crime site or a victim, identifying a perpetrator via a "cold hit" in a networked crime laboratory DNS database, identifying a victim or human remains, and proving the innocence, of wrongly incarcerated prisoners by analyzing archived evidence. Sample types and matrices can vary considerably, and the entire sample preparation process can be very time consuming and labor intensive.

Rape kits, containing swab samples of biological evidence collected in hospitals from victims of sexual assault, are amongst the most common, yet difficult, sample types to process since the swabs potentially contain a mixture of female epithelial cells and male sperm cells. Differential extraction is applied to separate the two distinct cell types into male and female cell lysate fractions, and extract and purify the DNA from each fraction. A resultant genetic profile of the male DNA is compared to that of a suspect, if available, or screened through the crime laboratory DNA database.

The conventional method for separating epithelial cells from sperm cells involves selective lysis using a combination of enzymes, chemicals, heat, and centrifugation. In a mixed sample, the epithelial cells are lysed first due to their lack of a protective coat, the sperm cells are pelleted using centrifugation, the epithelial cell lysate is removed, the sperm cells are re-suspended, and the sperm cells are lysed using more stringent enzymatic, chemical, and heat conditions. This conventional process takes hours, sometimes days. New cost-effective and efficient methods and instrumentation need to be developed and validated for practical low-cost, low processing time, high-throughput solutions.

SUMMARY OF THE INVENTION

In one aspect of the present invention, a method of selectively lysing a specific type of cell includes providing a sample including at least two different cell types, wherein a first cell type is lysed at a first sonication energy, applying the first sonication energy to the sample thereby lysing the first cell type to form a first lysate, separating the first lysate from the sample, and lysing a second cell type to form a second lysate. The second cell type can be lysed at a second sonication energy and lysing the second cell type comprises applying the second sonication energy to the sample. Lysing the second cell type can also include adding an additive to the sample prior to applying the second sonication energy. The first sonication energy can be lower than the second sonication energy. Lysing the second cell type can comprise applying a chemical treatment to the second cell type. The method can also include adding an additive to the sample prior to applying the first sonication energy. The first cell type can comprise an epithelial cell. The first cell type can comprise a virus, a microbe, or a spore. The second cell type can comprise a sperm cell. The second cell type can comprise a virus, a microbe, or a spore. The method can also include performing protein purification on the first lysate. The method can also include performing protein purification on the second lysate. The second cell type can remain intact after application of the first sonication energy. The sample can include N different cell types, each cell type is lysed at a different sonication energy. The method can also include applying a sonication energy corresponding to a particular cell type and separating the resulting lysate, and repeating the steps to generate N−1 lysates. Each successive application of sonication energy to the sample can utilize a sonication energy that is higher than the previous application. The method can also include adding an additive to the sample prior to one or more of the N−1 applications of the corresponding sonication energy. Applying the first sonication energy, separating the first lysate, and lysing the second cell type can be automated. The method can also include automating a protein purification of the first lysate. The method can also include automating a protein purification of the second lysate. Separating the first lysate from the sample can comprise using a filter that passes the first lysate and blocks the second cell type. Separating the first lysate from the sample can comprise performing centrifugation on the sample to form a sperm cell pellet and removing the first lysate. Providing a sample can comprise placing a sample matrix and applying a third sonication energy to the sample matrix to release the sample from the sample matrix.

In another aspect of the present invention, a method of selectively lysing a specific type of cell includes providing a sample including at least two different cell types, wherein a first cell type is lysed at a first sonication energy, automatically applying the first sonication energy to the sample thereby lysing the first cell type to form a first lysate, automatically separating the first lysate from the sample, and automatically lysing a second cell type to form a second lysate. The method can also include automating a protein purification of the first lysate. The method can also include automating a protein purification of the second lysate. Providing the sample can be automated. The second cell type can be lysed at a second sonication energy and automatically lysing the second cell type comprises automatically applying the second sonication energy to the sample. Automatically lysing the second cell type can also include automatically adding an additive to the sample prior to automatically applying the second sonication energy. Automatically lysing the second cell type can comprise automatically applying a chemical treatment to the second cell type. The method can also include automatically adding an additive to the sample prior to automatically applying the first sonication energy. The sample can include N different cell types, each cell type is automatically lysed at a different sonication energy. The method can also include automatically applying a sonication energy corresponding to a particular cell type and automatically separating the resulting lysate, and automatically repeating the steps N−1 times to generate N−1 lysates. Each successive application of sonication energy to the sample can utilize a sonication energy that is higher than the previous application. The method can also include automatically adding an additive to the sample prior to one or more of the N−1 applications of the corresponding sonication energy. Automatically separating the first lysate from the sample can comprise using a filter that passes the first lysate and blocks the second cell type. Automatically separating the first lysate from the sample can comprise automatically performing centrifugation on the sample to form a sperm cell pellet and removing the first lysate. Providing a sample can comprise placing a sample matrix and applying a third sonication energy to the sample matrix to release the sample from the sample matrix.

In yet another aspect of the present invention, an apparatus to selectively lyse a specific type of cell includes a sonication chamber to receive a sample and to provide a first sonication energy, the sample having at least two different cell types, wherein a first cell type is lysed at the first sonication energy to form a first lysate, a separating means to separate the first lysate from the sample, a collection vessel to collect the first lysate, and microfluidic circuitry to couple the sonication chamber, the separating means, and the collection vessel. The first cell type can comprise an epithelial cell. The first cell type can comprise a virus, a microbe, or a spore. The separating means can comprise a filter that passes the first lysate and block the remaining sample. The remaining sample can include a second cell type, the second cell type is lysed at a second sonication energy. Microfluidic circuitry can provide the remaining sample with the second cell type to the sonication chamber to be lysed. The sonication chamber can provide the second sonication energy to lyse the second cell type, thereby forming a second lysate. The apparatus can also include a purification chip coupled to the sonication chamber to receive the second lysate and collect a DNA from the second lysate. The apparatus can be automated. The second cell type can comprise a sperm cell. The apparatus can also include a second sonication chamber such that the microfluidic circuitry provides the remaining sample with the second cell type to the second sonication chamber to be lysed. The second sonication chamber can provide the second sonication energy to lyse the second cell type, thereby forming a second lysate. The apparatus can also include a purification chip coupled to the second sonication chamber to receive the second lysate and collect a DNA from the second lysate. The apparatus of can also include a purification chip to receive the lysate and collect a DNA from the lysate. The sample can include N different cell types, each cell type is lysed at a different sonication energy. The apparatus can also include N−1 or less additional sonication chambers to apply N−1 or less different sonication energies to the corresponding N−1 or less different cell types. The apparatus can also include N or less purification chips to receive N or less lysates from the N or less sonication chambers. The separating means can comprise means for performing centrifugation on the sample to form a sperm cell pellet. The sonication chamber can provide a third sonication energy to a sample matrix, thereby releasing the sample from the sample matrix.

DETAILED DESCRIPTION OF THE PRESENT INVENTION

Embodiments of a sonication apparatus of the present invention are directed to a microfluidic-based system to automate differential extraction of specific cell types within a mixed sample. The microfluidic-based system includes a sonication module for selective cell lysis, separating means to eliminate centrifugation, high surface area pillar chip modules to purify DNA from a cell lysate, and microfluidic circuitry to integrate the steps in an automated platform.

The sonication module can include one or more sonication chambers. In the preferred embodiment, the sonication module includes two sonication chambers. Alternatively, one sonication chamber can be used. Still alternatively, three or more sonication chambers can be used when a mixed sample includes three or more different cell types. Each of these sonication module configurations is discussed in greater detail below.

Conventional sonication is an established physical method for rapid and non-specific lysing of cells and viruses. As applied in the present invention, sonication is used to selectively lyse cells and viruses. Sonication amplitude, duration, and frequency can be adjusted to lyse certain cell types or viruses without lysing other cell types or viruses in a mixed sample. In addition, sonication can be used in combination with chemical and enzymatic approaches to further achieve higher cell or virus lysis specificity. Other additives such as glass beads can also be combined with the sonication and/or chemical and enzymatic approaches.

In one exemplary application, forensic rape kit samples typically include sperm cells and female epithelial cells. In forensic applications, embodiments of the present invention provide an automated, microfluidic system for differential extraction of samples having a mixture of female epithelial cells and male sperm cells. The sonication apparatus of the present invention preferably includes a sonication module for selective cell lysis and a silicon chip module for rapid DNA extraction, purification, and concentration. This sonication apparatus is a turn-key system in which an operator loads samples starts the apparatus, and allows the sonication apparatus to run unattended while performing the entire differential extraction method. In an alternative embodiment, the sample loading process is also automated.

In conventional methods, a mild 2 hour enzymatic/chemical step is first used to lyse the softer epithelial cells. The sperm cells are pelleted by centrifugation and the epithelial cell lysate is removed. The sperm cells are re-suspended and subjected to a strong 2 hour enzymatic/chemical step to lyse the tougher sperm cells. In the present invention, a few minutes of low amplitude sonication replaces the mild 2 hour enzymatic/chemical step and a few minutes of high amplitude sonication replaces the strong enzymatic/chemical step. Alternative separating means can also be used in place of the centrifugation to separate the epithelial cell lysate from the intact sperm cells.

The present invention provides many advantages over conventional lysing methods. The method of the present invention is much faster than chemical and enzymatic approaches, the method is more repeatable, the method provides improved cell or virus lysis selectively, and the method is amenable to automation using robotics and/or microfluidics. In the preferred embodiment, sonication chambers and separating means are embedded in a microfluidic system.

In the preferred embodiment, each sonication chamber is of the type described in U.S. Pat. No. 6,100,084. The preferred sonication chamber includes a container with a cavity therein for retaining a sample in an ultrasonic transmission medium. The cavity is closed using a membrane. An electrode and a piezoelectric material are attached to the membrane, and a voltage source is electrically connected to the electrode and the piezoelectric material. An amount of sonication energy necessary to lyse a specific cell type is a function of many factors including, but not limited to, the amount of voltage applied to the membrane, the thickness of the membrane, the dimensions of the container and the cavity, the material of the container, the material of the membrane, a composition of the transmission medium within the cavity, a duration of the applied voltage, and the type of cell to be lysed. As such, the sonication energy required to lyse a specific cell type is experimentally determined and in general is a relative function of the equipment used. As used herein, the term "sonication energy" is used to define an energy amplitude, frequency, duration, or any combination thereof. Use of the preferred sonication chamber provides the ability to regulate the applied sonic energy with high precision.

The microfluidic system includes microfluidic circuitry to process small liquid volumes for complex reagent metering, mixing, and biochemical analysis. The microfluidic system provides a closed-loop environment which minimizes environmental contamination and the potential of compromising the integrity of the sample.

Figure 1:
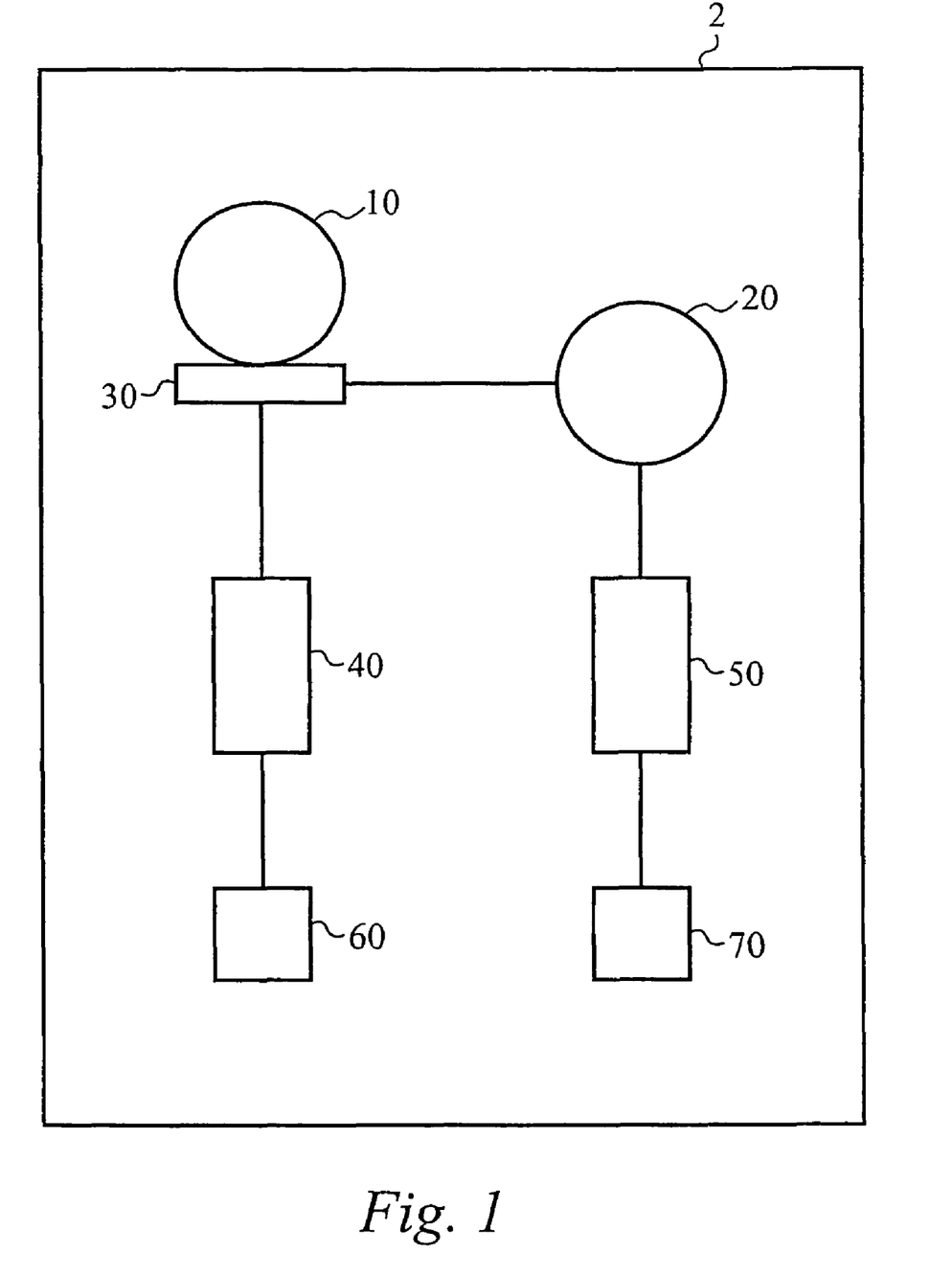
FIG. 1 illustrates a conceptual block diagram of a sonication apparatus to selectively lyse a mixed sample using sonication according to the preferred embodiment of the present invention.

FIG. 1 illustrates a conceptual block diagram of a sonication apparatus 2 to selectively lyse a mixed sample using sonication according to the preferred embodiment of the present invention. The mixed sample preferably includes at least two different cell types. For example, the sample can be a rape kit sample that includes female epithelial cells and male sperm cells. A first cell type within the mixed sample is lysed at a first sonication energy, and a second cell type is lysed at a second sonication energy. The apparatus 2 includes a first sonication chamber 10, a second sonication chamber 20, a separating means 30, a first purification chip 40, a second purification chip 50, a first output vessel 60, and a second output vessel 70, each of which is preferably coupled using microfluidic circuitry, which is discussed in greater detail below. The mixed sample is placed in the first sonication chamber 10. The first sonication chamber 10 provides the first sonication energy to the mixed sample, thereby lysing the first cell type. The first sonication energy used to lyse the first cell type is preferably lower than the second sonication energy necessary to lyse the second cell type. As a result, after the first sonication energy is applied to the sample, the sample includes the first cell type lysate, referred to as a first lysate, and the second cell type which is still intact. The separating means 30 separates the first lysate from the mixed sample. The first lysate passes through the separating means 30 and is directed to the first purification chip 40. The separating means 30 preferably includes pores or openings that each have a diameter that is less than the diameter of the intact second cell type. Separation of a lysate from a sample is performed using any conventional separating means. Examples of such separating means include, but are not limited to, a filter, a membrane, magnetic beads, a frit, or any other means for separating a lysate from an intact cell type. The intact second cell type is blocked by the separating means 30 and is preferably directed to the second sonication chamber 20 by back flowing a buffer through the separating means 30.

The first purification chip 40 purifies and concentrates DNA from within the first lysate such that a first DNA is collected and the remaining portion of the first lysate passes through as waste. The collected first DNA is collected in the first output vessel 60.

The second sonication chamber 20 provides the second sonication energy used to lyse the second cell type. The resulting second lysate is preferably directed to the second purification chip 50. The second purification chip 50 purifies and concentrates DNA from within the second lysate such that a second DNA is collected and the remaining portion of the second lysate passes through as waste. The collected second DNA is collected in the second output vessel 70. Each of the purification chips 40 and 50 are preferably of the type described in U.S. Pat. No. 5,707,799 and U.S. Pat. No. 5,952,173, which are both hereby incorporated by reference.

Although the preferred sonication apparatus 2 is illustrated and described in terms of selectively lysing two different cell types, it is understood that the mixed sample can include more than two different cell types and that the sonication apparatus can selectively lyse more than two cell types. In this case, the number of sonication chambers used is determined by the number of anticipated different cell types to be lysed. Each cell type to be lysed must be lysed at a different sonication energy than the other cell types within the mixed sample. If two cell types are lysed at the same sonication energy, then it is not possible to lyse one without lysing the other using this sonication method. However, cell types that are uniquely lysed at a given sonication energy can be selectively lysed using this sonication method.

In an alternative embodiment, lysing of particular cell types can be facilitated by adding additives to the sample prior to any of the sonication steps. As with empirically determining the specific sonication energy required to lyse a particular cell type, the proper type and amount of additives to be used is also determined experimentally. Examples of additives include glass beads, chemicals, enzymes, or the addition of heat.

In still another alternative embodiment, the last remaining cell type in the original mixed sample can be lysed using conventional chemical and/or enzymatic lysing methods. For example, where a mixed sample includes two different cell types to be lysed, the first cell type is lysed using the aforementioned sonication method at the first sonication energy, and the second cell type is lysed using a chemical/enzymatic lysing method. As another example, where a mixed sample includes three different cell types, two of the cell types can be selectively lysed as described above in relation to the sonication apparatus 2. The third cell type can be lysed using any conventional lysing method, including sonication, chemical, or enzymatic.

Multiple sonication apparatuses 2 can also be coupled together in parallel. In such a configuration, multiple mixed samples can be processed in parallel to increase throughput.

Figure 2:
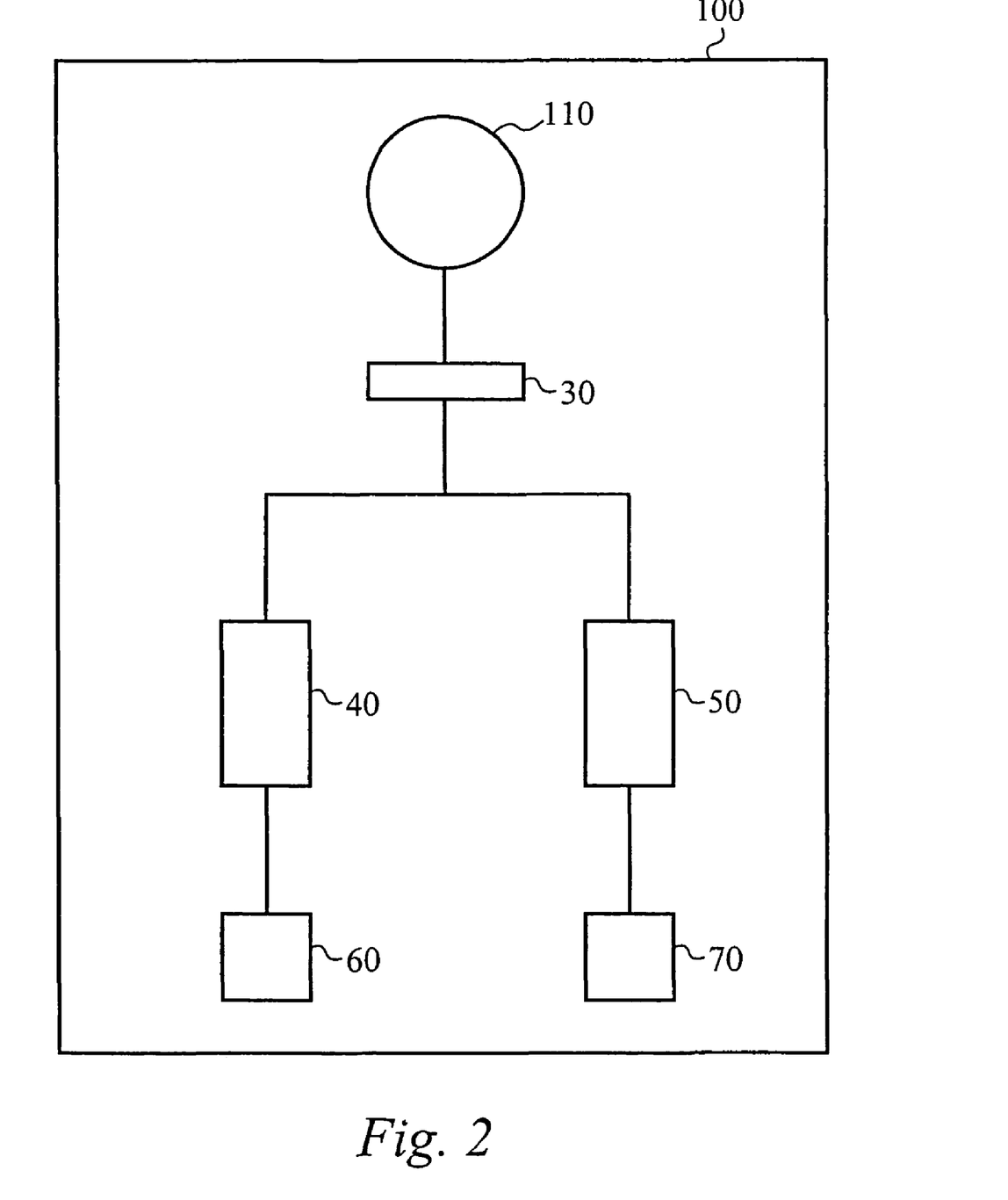
FIG. 2 illustrates a conceptual block diagram of a sonication apparatus to selectively lyse a mixed sample using sonication according to a first alternative configuration.
Figure 3:
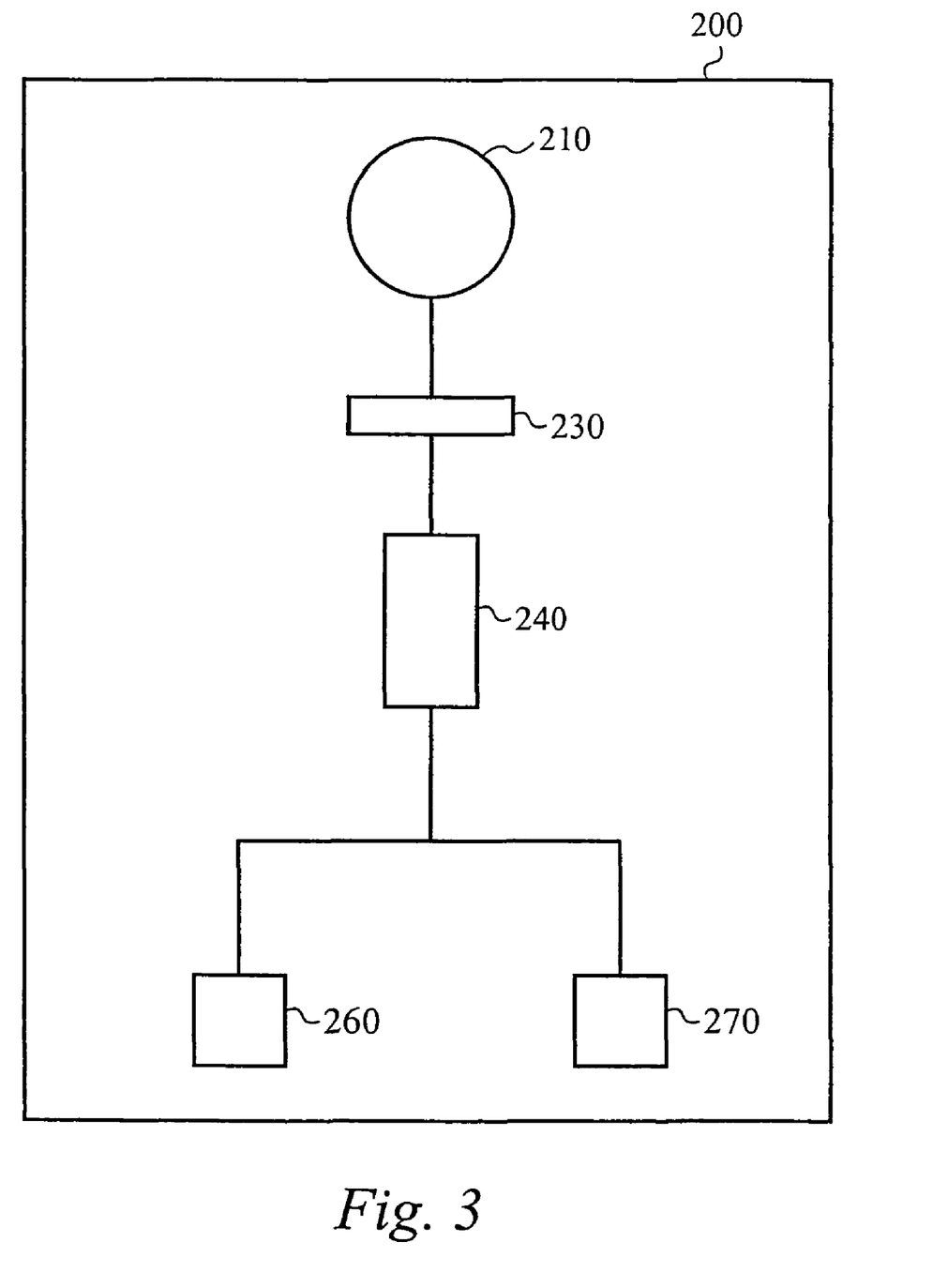
FIG. 3 illustrates a conceptual block diagram of a sonication apparatus to selectively lyse a mixed sample using sonication according to a second alternative configuration.

It is also understood that various alternative combinations of sonication chambers, separating means, and purification chips can be used to selectively lyse different cell types and to collect DNA from the resulting lysates. FIGS. 2 and 3 illustrate two such alternative configurations.

FIG. 2 illustrates a conceptual block diagram of a sonication apparatus 100 to selectively lyse a mixed sample using sonication according to a first alternative configuration. The alternative sonication apparatus 100 operates similarly to the preferred sonication apparatus 2 except that the two sonication chambers 10 and 20 are replaced by a single sonication chamber 110. In operation, the first sonication chamber 110 receives the mixed sample and the first sonication energy is applied, thereby lysing the first cell type and producing the first lysate. The first lysate is separated from the mixed sample by the separating means 30, such that the first lysate passes through the separating means 30 and the intact second cell type is blocked by the separating means 30. The first lysate is directed to the first purification chip 40 as described above in relation to the preferred sonication apparatus 2. The blocked second cell type is back flushed from the separating means 30 to the sonication chamber 110. The sonication chamber 110 applies the second sonication energy to the second cell type, thereby lysing the second cell type to produce the second lysate. The second lysate is directed to the second purification chip 50 as described above in relation to the preferred sonication apparatus 2.

FIG. 3 illustrates a conceptual block diagram of a sonication apparatus 200 to selectively lyse a mixed sample using sonication according to a second alternative configuration. The second alternative sonication apparatus 200 includes a single sonication chamber 210 and a single purification chip 240. The sonication chamber 210 receives the mixed sample and provides the first sonication energy as described in detail above. The first lysate passes through the separating means 230 to the purification chip 240. The purification chip 240 purifies and concentrates the first DNA from within the first lysate and the remaining portion of the first lysate passes through as waste. The collected first DNA is flushed from the purification chip 240 and is collected in the first output vessel 260. Flushing the first DNA also acts to clean the purification chip 240. Alternatively, after the first DNA is flushed from the purification chip 240 to the first output vessel 260, a cleaning step is performed in which the purification chip 240 is rinsed with a cleaning solution to remove any remaining first lysate. The cleaning solution and any accompanying waste is removed from the sonication apparatus 200 using the microfluidic circuitry included therein.

The separating means 230 blocks the intact second cell type and the intact second cell type is collected in the sonication chamber 210. The second sonication energy is provided by the sonication chamber 210, thereby lysing the second cell type. The second lysate passes through the separating means 230 into the purification chip 240. The second DNA is purified and collected within the purification chip 240 while the remaining portion of the second lysate passes through as waste. The collected second DNA is collected in a second output vessel 270.

It is understood that multiple first alternative sonication apparatuses 100 can be coupled together in parallel, and that multiple second alternative sonication apparatuses 200 can be coupled together in parallel. Further, one or more sonication apparatuses 2, one or more sonication apparatus 100, and/or one or more sonication apparatuses 200 can be coupled together in parallel to simultaneously process multiple mixed samples.

Each sonication apparatus 2, 100, and 200 are preferably configured as microfluidic cassettes. A microfluidic cassette avoids the necessity of complicated, expensive robotic devices, while improving the effectiveness and efficiency of fluid metering, mixing, and dispensing. The cassette can include a multilayer microfluidic plastic block with fluidic circuitry and multiple independent active valves, syringe drives, a sonication lysis module including one or more sonication chambers as described above, one or more DNA purification chips, reagent reservoirs, electronic hardware, and custom user interface. Fluid flow through the microfluidic cassette can be pressure-driven and computer-controlled. As such, each sonication apparatus can be completely automated.

The microfluidic cassette can include a liquid-handling module and a pneumatic module. Each of these modules can be comprised of several layers of machined polycarbonate plastic parts, which are sandwiched and sealed together using laser cut sheets of silicone gasket material. The silicone gasket material serves to seal the layers in each module and also to function as diaphragm valves in the liquid-handling module. Tens to hundreds of independently controlled valves, working systematically to direct the flow of sample and reagents, can be created.

Syringe pumps can be used as a drive mechanism for moving, mixing, aspirating, and dispensing boluses of liquid between locations in the liquid-handling block. The syringe driver boards control a stepper motor that moves the syringe plungers. Since the full stroke of the syringes has 48,000 steps, high precision fluid metering can be accomplished. For example, the resolution for displacement of fluid using a 1 ml syringe barrel is 0.0208 ul per step. A variety of syringe sizes can be incorporated to accommodate fast, large volume movement and precise small volume metering.

Peristaltic pumps can also be used as the drive mechanism. The peristaltic pump can achieve continuous flow and minimizes problems of air in the lines.

The liquid-handling module can be mounted on the pneumatic module with o-rings around each pressure outlet to seal the pneumatic path. Valves in the liquid-handling module are opened and closed by electrical actuation of three-way solenoid valves mounted on the backside of the pneumatic module. The liquid-handling module preferably include inlet and outlet ports, microchannels, mixing chambers, at least one sonication chamber, and at least one DNA purification chip.

Solutions and reagents can be included within the cassette, or they can be introduced from lines connected to external bulk containers.

A simple and intuitive Graphical User Interface (GUI) offers control to the system hardware components. The GUI enables a user to fully control the syringe drive motion and speed, and all the pneumatically actuated membrane valves. The GUI also enables the user to script, store, load, and run protocols, which can be edited and modified throughout the course of protocol optimization.

The microfluidic cassette can be configured to process multiple samples simultaneously. In one embodiment, the cassette can process 10 samples simultaneously per run. If one run takes 30-45 minutes, then up to 480 samples can be processed in a 24 hour period. The automation process can be extended to use an automated feeder of samples to the microfluidic cassette.

The microfluidic cassette can also include a DNA purification module. The DNA purification module preferably uses a DNA purification chip. The purification chip is preferably embedded in the plastic microfluidic cassette. The purification chip is preferably a micromachined silicon structure having micropillars. The micropillars create a high surface area within a collection chamber. Nucleic acids are captured on the pillars, washed, and released in a small elution volume using standard chaotropic salt chemistry. Advantages to this flow through process include amenability to a system integration in a microfluidic platform and rapid extraction of nucleic acids from large volume samples. In addition, the high concentration effect permits using less sample and consequently less PCR (Polymerase Chain Reaction) reaction mix for PCR amplification.

Another advantage of the micropillar chip for DNA purification and concentration is the ability to produce compact arrays of these chips for high throughput purification. An array of purification chips can be harbored in a microfluidic circuit. Each chip can have a dedicated line and essentially be isolated form one another. Such a configuration can be accomplished using microfluidics in which an intricate network of channels is confined to a relatively small area. Such an array can have broad applications for preparing DNA from a wide variety of sample types. An exemplary array of DNA purification chips includes an 8×12 array of 96 micropillar chips.

Figure 4:
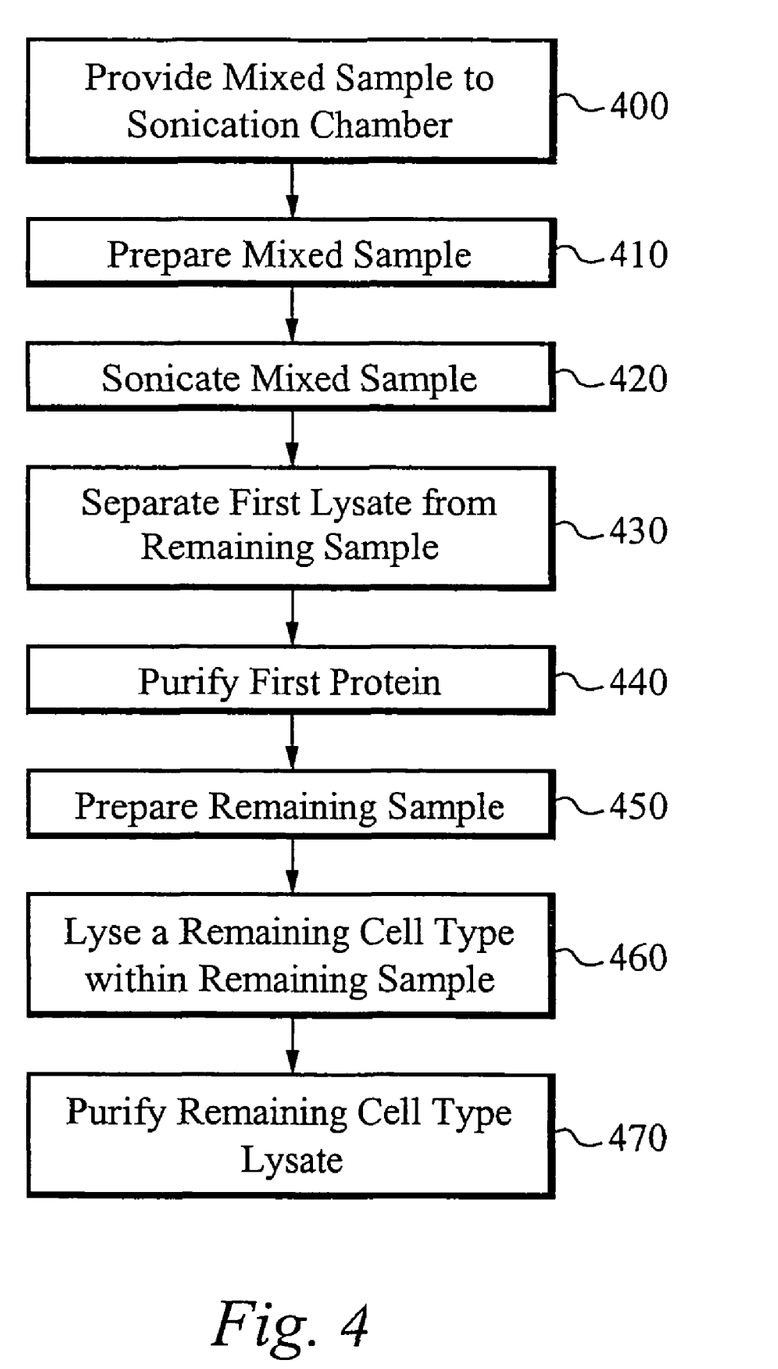
FIG. 4 illustrates a general method of performing selective lysis and protein purification.

FIG. 4 illustrates a general method of performing selective lysis and protein purification. At a step 400, a mixed sample is provided to a sonication chamber. The mixed sample preferably has two or more different cell types, each cell type is lysed at a different sonication energy. For example, a first cell type lyses at an associated first sonication energy, a second cell type lyses at an associated second sonication energy, and so on. At a step 410, a buffer solution is added to the mixed sample within the sonication chamber. At a step 420, a first sonication energy is applied to the mixed sample, thereby lysing a first cell type within the mixed sample. After sonication, the mixed sample comprises a first lysate, which is the lysed first cell type, and a remaining portion of the mixed sample. The remaining portion of the mixed sample includes intact cells for each cell type that has a sonication energy greater than the first sonication energy already applied.

At a step 430, the first lysate is separated from the mixed sample. Preferably, the separating means allows the first lysate to pass while blocking the remaining portion of the mixed sample. At a step 440, the first lysate is passed through a purification chip to purify and concentrate a first protein included within the first lysate. The first protein is collected within the purification chip while a remaining portion of the first lysate passes through the purification chip as waste. The first protein collected in the purification chip is preferably flushed and collected as a first purified protein sample.

Additional cell types in the remaining mixed sample can also be lysed. If a single remaining cell type is in the remaining mixed sample, then the remaining cell type can be lysed either using sonication or using a conventional lysing method such as a chemical and heat combination. If more than one different cell type remain in the remaining sample mixture, than the steps 410 through 440 are repeated for each remaining cell type starting with the cell type with the lowest lysing sonication energy and working upward. Again, the last remaining cell type can be lysed using sonication or other conventional lysing method.

At a step 450, a last remaining cell type within the remaining mixed sample is prepared for sonication. Preferably, the last remaining cell type is lysed using sonication. In this preferred case, a buffer solution is added to the remaining mixed sample in preparation for sonication. Alternatively, the last remaining cell type is lysed using a conventional lysing method. In this alternative case, chemical additives are added to the remaining mixed sample. At a step 460, the remaining cell type is lysed to form a final lysate. At a step 470, the final lysate is passed through a purification chip to purify and concentrate a final protein included within the final lysate. The final protein is collected within the purification chip while a remaining portion of the final lysate passes through the purification chip as waste. The final protein collected in the purification chip is preferably flushed and collected as a final purified protein sample.

Figure 5:
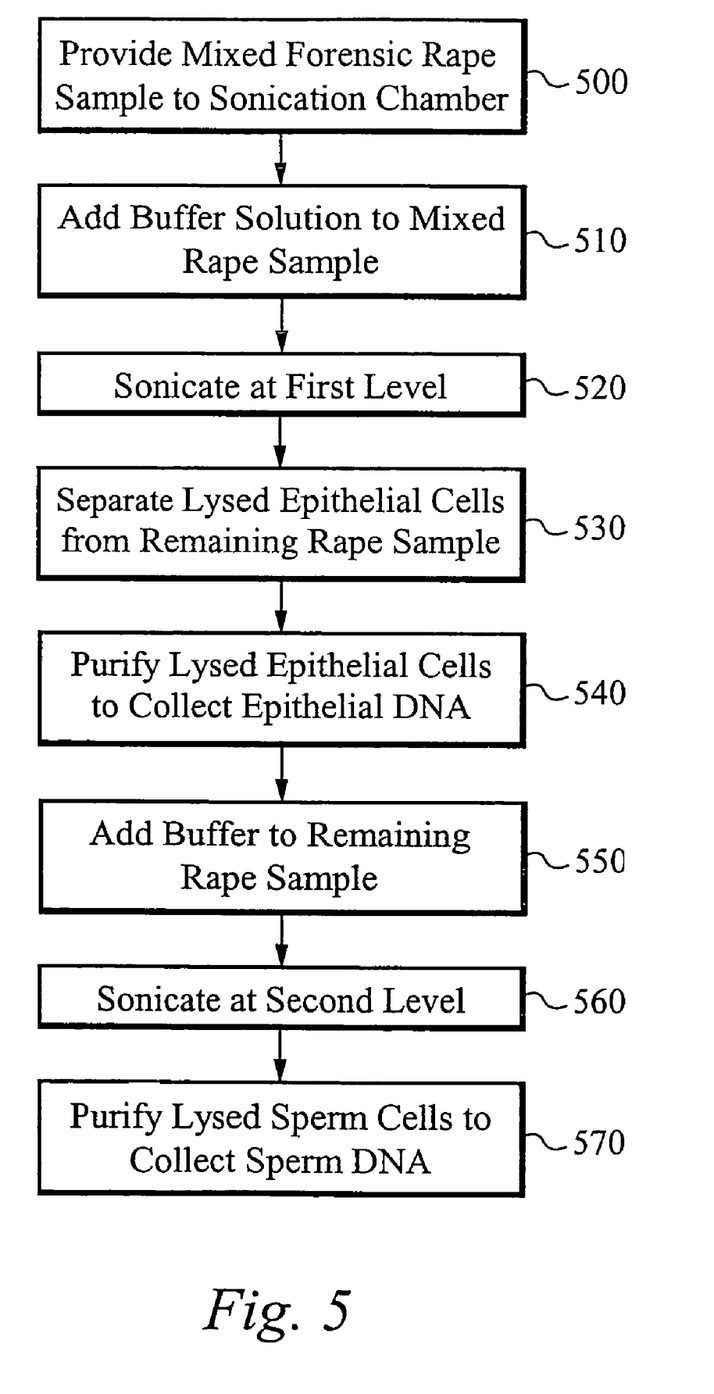
FIG. 5 illustrates an exemplary method in which a sonication apparatus of the present invention is applied to a rape kit.

FIG. 5 illustrates an exemplary method in which a sonication apparatus of the present invention is applied to a rape kit. In such an application, the rape kit includes a mixed forensic rape sample having female epithelial cells and male sperm cells on a matrix. The matrix can include a swab or a swatch. It is desired to isolate the male DNA from the sperm cells, the female DNA from the epithelial cells, or both. In the preferred embodiment, two sonication steps are included. A first sonication step uses a mild treatment to lyse epithelial cells but not sperm cells. A second sonication step uses a harsh treatment to lyse sperm cells. In an alternative embodiment, a chemical/heat treatment step is implemented to lyse the sperm cells, thereby eliminating the requirement for a second sonication chamber on the integrated platform.

In a step 500, the swab or swatch with the mixed rape sample is placed in the sonication chamber. At a step 510, a buffer solution is added to the mixed rape sample. Preferably, the buffer solution is a 0.5-1 ml 10 mM Tris-HCL with a pH of about 8.0. Alternatively, the buffer solution is water. Still alternatively, the sonication chamber also includes glass beads. It is understood that the steps 500 and 510 can be reversed such that the sonication chamber already includes the buffer solution prior to adding the mixed rape sample. At a step 520, a first sonication energy is applied to the mixed rape sample. As described above, the specific amount of sonication energy necessary to lyse the epithelial cells is dependent on the specifications of the particular sonication chamber used. Application of the first sonication energy releases both the epithelial cells and the sperm cells from the matrix into the buffer solution. The first sonication energy is sufficient to selectively lyse the epithelial cells, however the more durable sperm cells remain intact. Sonication at the first sonication energy is considered a mild sonication. After application of the first sonication energy, the buffer solution includes the lysed epithelial cells and intact sperm cells.

At a step 530, the swab or swatch is preferably removed and the lysed epithelial cells are separated from the intact sperm cells. The separating means preferably includes a filter with pores or openings each with a diameter of about 2 um. The sperm cells, which have about a 5 um diameter, are blocked by the separating means, while the lysed epithelial cells pass through the separating means to a female collection vessel. In general, the diameter of the filter pores or openings is large enough to allow the epithelial cell lysate to pass, but small enough to prevent the intact sperm cells from passing. The sonication chamber is preferably rinsed with buffer to move the epithelial cell lysate through the separating means. At a step 540, the lysed epithelial cells are preferably mixed with an equal volume of bind solution and passed through a purification chip where the female epithelial DNA is purified and concentrated from the remaining epithelial cell lysate. The remaining epithelial cell lysate passes through the purification chip as waste. The epithelial cell DNA is collected from the purification chip.

At a step 550, the intact sperm cells are back flushed from the separating means to a second sonication chamber and a 0.2 molar NaOH, or basic solution, is added. Alternatively, the intact sperm cells are back flushed from the separating means to the sonication chamber where the epithelial cells were previously lysed. The NaOH solution preferably includes 50 mM DTT. Alternatively, proteinase K can also be added to the preferred basic solution. At a step 560, a second sonication energy is applied to lyse the sperm cells. The second sonication energy is greater than the first sonication energy used to lyse the epithelial cells. Sonication at the second sonication energy is considered a harsh sonication. At a step 570, the lysed sperm cells are passed through the separating means and directed a second purification chip. Alternatively, the lysed sperm cells can first be collected in a male collection vessel, and later directed to the second purification chip. The lysed sperm cells are preferably mixed with an equal volume of bind solution and passed through the second purification chip where the male sperm DNA is purified and concentrated from the remaining sperm cell lysate. The remaining sperm cell lysate passes through the purification chip as waste. The sperm DNA is collected from the purification chip. Alternatively, a single purification chip is used to collect both the epithelial DNA and the sperm DNA. In some applications, DNA purification is not required and the collected intact sperm can be removed from the sonication apparatus prior to application of the second sonication energy.

In an alternative embodiment, the male sperm cells can be lysed by methods other than sonication. For example, instead of performing the steps 550 and 560, the intact sperm cells are collected in a male collection vessel, basic solution is added, and the male collection vessel is heated to a predetermined temperature for a predetermined duration to lyse the male sperm cells.

In another alternative embodiment, after the first sonication, the intact sperm cells are separated from the epithelial cell lysate by subjecting the mixture to centrifugation. The epithelial cell lysate is removed from the sperm cell pellet. The sperm cell pellet is re-suspended and subjected to sonication at the second sonication energy to lyse the sperm cells. It should be understood that alternative separating means can be used, as described above.

As previously discussed, a systematic approach is taken to develop the most appropriate protocol for the differential extraction method. First, sonication threshold levels for sperm cells and epithelial cells are determined. It is known that sperm cells are more resistant to sonication than epithelial cells. DTT is known to break down the disulfide bonds in the sperm coat. Sonication with the addition of DTT can be used to facilitate sperm cell lysis. A typical procedure for spore lysis uses glass beads during sonication, and although the use glass beads during sonication does lyse sperm cells, glass beads are preferably avoided for sperm cell lysis. Selective lysis of the epithelial cells is preferably accomplished using mild sonication without DTT.

It should be understood that the lysates can be purified using means other than the described purification chips. For example, the epithelial and sperm cell lysates can be subjected to DNA purification using the purification chip, glass membrane, glass column, organic extraction, ethanol precipitation, or any other method known to purify nucleic acids.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. An apparatus to selectively lyse a specific type of cell, the apparatus comprising:
   a. a sonication chamber to receive a sample and to provide a first sonication energy, the sample having at least two different cell types, wherein a first cell type is lysed at the first sonication energy, further wherein the sonication chamber is configured to selectively lyse the first cell type, thereby forming a first lysate, while leaving one or more non-lysed cell types within a remaining sample;
   b. separating means to separate the first lysate from the sample;
   c. a collection vessel to collect the first lysate; and
   d. microfluidic circuitry to couple the sonication chamber, the separating means, and the collection vessel, wherein the microfluidic circuitry is configured to enable backflow capability for moving the remaining sample including the one or more non-lysed cell types from the separating means to the sonication chamber, further wherein the sonication chamber is configured to lyse a second cell type within the remaining sample.

2. The apparatus of claim 1 wherein the first cell type comprises an epithelial cell.

3. The apparatus of claim 1 wherein the first cell type comprises a virus, a microbe, or a spore.

4. The apparatus of claim 1 wherein the separating means passes the first lysate and blocks the remaining sample.

5. The apparatus of claim 4 wherein the second cell type is lysed at a second sonication energy.

6. The apparatus of claim 5 wherein the sonication chamber provides the second sonication energy to lyse the second cell type, thereby forming a second lysate.

7. The apparatus of claim 6 further comprising a purification chip coupled to the sonication chamber to receive the second lysate and collect a DNA from the second lysate.

8. The apparatus of claim 7 wherein the apparatus is automated.

9. The apparatus of claim 5 wherein the second cell type comprises a sperm cell.

10. The apparatus of claim 1 further comprising a purification chip to receive the first lysate and collect a DNA from the first lysate.

11. The apparatus of claim 10 wherein the apparatus is automated.

12. The apparatus of claim 1 wherein the sample includes N different cell types, each cell type is lysed at a different sonication energy.

13. The apparatus of claim 12 wherein the sonication chamber is configured to apply N different sonication energies to the corresponding N different cell types.

14. The apparatus of claim 13 further comprising N purification chips to receive N lysates from the sonication chamber.

15. The apparatus of claim 1 wherein the separating means comprises means for performing centrifugation on the sample to form a sperm cell pellet.

16. The apparatus of claim 1 wherein the sonication chamber provides a third sonication energy to a sample matrix, thereby releasing the sample from the sample matrix.

* * * * *